United States Patent [19]

Shaldon et al.

[11] Patent Number: 4,498,990
[45] Date of Patent: Feb. 12, 1985

[54] FILTERING DEVICE

[75] Inventors: Stanley Shaldon, Montpellier, France; Kjell H. I. Christopherson, Staffanstorp, Sweden; Thore E. Falkvall, Viken, Sweden; Ulf K. Mattisson, Sodra Sandby, Sweden

[73] Assignee: Gambro Lundia AB, Sweden

[21] Appl. No.: 399,970

[22] Filed: Jul. 19, 1982

[30] Foreign Application Priority Data

Oct. 5, 1981 [SE] Sweden ............................ 8105850

[51] Int. Cl.³ ............................................. B01D 13/00
[52] U.S. Cl. ................................... 210/637; 210/641; 210/259; 210/433.2
[58] Field of Search ............... 210/450, 433.2, 130, 210/638, 641, 259, 90, 637, 110

[56] References Cited

U.S. PATENT DOCUMENTS

| 2,731,154 | 1/1956 | Burnell | 210/130 |
| 2,734,636 | 2/1956 | Foster | 210/130 |
| 3,228,877 | 1/1966 | Mahon | 210/638 |
| 3,331,509 | 7/1967 | Gray, Jr. | 210/90 |
| 3,776,842 | 12/1973 | Grimme, Jr. | 210/259 X |
| 4,064,052 | 12/1977 | Zimmerly | 210/433.2 |
| 4,301,013 | 11/1981 | Setti et al. | 210/433.2 X |
| 4,350,594 | 9/1982 | Kawai et al. | 210/641 X |
| 4,397,747 | 8/1983 | Ikeda | 210/110 X |

OTHER PUBLICATIONS

Porter et al., "Membrane Ultrafiltration", from Chem. Tech., 1-1971, 8 pages.

Primary Examiner—Frank Spear
Attorney, Agent, or Firm—Lerner, David, Littenberg, Krumholz & Mentlik

[57] ABSTRACT

A filtering device is disclosed which includes a pressure sensitive control valve to allow for overflow. The filtering device is particularly suitable for use in the medical treatment of blood, e.g., hemofiltration and plasmapheresis.

28 Claims, 9 Drawing Figures

FILTERING DEVICE

BACKGROUND OF THE INVENTION

The present invention relates to a filtering device and a pressure sensitive valve therefor. Such a filtering device can be advantageously used in the medical treatment of blood, e.g., hemofiltration and plasmapheresis, which are methods of thickening blood and consequently a pressure drop occurs.

Hemofiltration refers to a process wherein the blood fluid is withdrawn from the patient together with toxins which could not be removed by means of the normal renal function. A quantity of liquid on the order of magnitude of 20 liters is withdrawn from the patient. It is desirable to supply back to the patient substantially the same quantity of replacement liquid, since a certain reduction in weight is not usually desired.

Plasmapheresis refers to a process wherein only the blood plasma is withdrawn from the blood donor, and the blood cells and similar larger molecules together with a small portion of the blood plasma are returned. In this process, a certain quantity of replacement liquid also may be supplied to the patient.

Both hemofiltration and plasmapheresis take place appropriately with the help of membrane filtration in devices which resemble normal membrane dialyzers. Usually, however, more permeable membranes and higher pressures are used than with dialysis. Moreover, no dialysis liquid is employed on the side of the membrane remote from the blood.

Normally, separate filtering devices are used for processes of the above-mentioned type which are thus similar to normal membrane dialyzers. Tests have also been carried out with filtering devices coupled in paralled or in series. One such device comprises an inlet and an outlet for the liquid filtered and an outlet for the filtrate, the filtration being arranged to take place in two chambers connected in series, which chambers consist at least partially of membrane material through which the filtration is taking place. A series connection in combination with an increase in pressure drop is especially suitable, since the latter gives an increase in the amount of filtrate. However, if the pressure drop across the filtering device is too great, problems may arise. For example, the blood may be damaged through hemolysis.

Experiments have also been carried out with chambers connected in series and in parallel arranged in one and the same casing, see, for example, U.S. Pat. No. 4,038,190. Difficulties may be experienced, however, with the designs described in this patent, if, in particular for hemofiltration or plasmapheresis, a sufficiently high pressure is to be achieved without the risk of too high a pressure when, for example, the filter becomes choked.

SUMMARY OF THE INVENTION

It has now been found in accordance with the present invention that the above-mentioned disadvantages are overcome by a filtering device comprising an inlet for the liquid to be filtered, means for filtering the liquid to be filtered to form a filtered liquid and a filtrate, a first outlet for the filtrate, a second outlet for the filtered liquid, and a pressure sensitive valve between the inlet and the second outlet so that undesired pressure build-up at the inlet results in at least some of the liquid to be filtered passing from the inlet to the second outlet. Preferably, the means for filtering comprises two chambers connected in series, wherein the chambers comprise membrane material through which filtration takes place.

The filtering device in accordance with the invention may be of the so-called plane film type, or it may consist of a membrane tube wound into a spiral. In a preferred embodiment, the filter means is of the fibrous type, with both chambers being arranged in one and the same casing and with each chamber being formed of a number of interior spaces of thin-walled fibers. In filtering devices of this type, a relatively high pressure can be used, while the risk of a leakage through membrane ruptures remains small.

The fibers of the two chambers may be cast in a conventional manner into two end walls of a cylindrical casing. The end walls are closed with outer covers bearing the inlet and the first outlet for the filtered liquid. In this connection, it has been found in accordance with the present invention that the inlet and the outlet for the filtered liquid can be suitably arranged in one of the outer covers, separated by a seal between the adjoining end wall and the corresponding outer cover. The seal thus constitutes the pressure-sensitive overflow valve. This principle permits different simple design solutions for the flow valve.

The seal may be ring-shaped, for example, and may be arranged substantially concentrically on the inside of the outer cover pressing against the outside of the adjoining end wall. The fibers cast into the end walls open out on the outside of these walls and are divided in this manner into two groups, each group forming the aforementioned two chambers.

To prevent the seal from stopping up some of the fibers, it is appropriate to cast a prop ring in the end wall in front of the seal.

In one embodiment of the invention, a simple design is achieved by employing an elastic ring as the seal. The elastic ring can be slipped onto a rigid flange fixed on the inside of the outer cover. In this rigid flange there may be one or more ports or windows. These ports are partly covered on their one side (the side toward the inlet) by the elastic ring. The elastic ring, however, wholly but resiliently covers the other side (the side toward the outlet for the filtered liquid) of the ports. The elastic ring is preferably given a U-shaped cross-section with one leg longer than the other. In this manner the shorter leg is the one that partly covers the ports on the one side and the longer leg is the one that wholly covers the ports on the side toward the outlet for the filtered liquid.

In another embodiment, the seal may be formed by a fixed ring arranged between the outer cover and the adjoining end wall. The fixed ring is provided with one or more radial ports of windows. The outside (the side toward the outlet for the filtered liquid) of the ports is covered by an elastic ring slipped onto the fixed ring. This elastic ring may be arranged in a peripheral groove in the fixed ring. By a suitable choice of the size or elasticity of the elastic ring, it is possible for the ports or windows to open at a certain predetermined maximum pressure, which thus allows overflow from the inlet to the outlet for the filtered liquid when such maximum pressure is exceeded.

The fixed ring is preferably attached to the adjoining end wall or the prop ring cast into such end wall, e.g., by gluing. An elastic sealing ring is appropriately arranged between the such fixed ring and the corresponding adjoining outer cover to seal the fixed ring to the outer cover.

In accordance with a further embodiment, the seal may be formed by an elastic ring comprising wall portions which tightly adhere to one another at a first lower pressure, but which are adapted so as to be separated as a second predetermined higher pressure to allow overflow to pass from the inlet to the outlet for the filtered liquid.

BRIEF DESCRIPTION OF DRAWINGS

The invention will be described in more detail with reference to the enclosed drawings, which by way of example show a number of different preferred embodiments of the invention, in which.

DETAILED DESCRIPTION OF THE INVENTION

Figure 1:
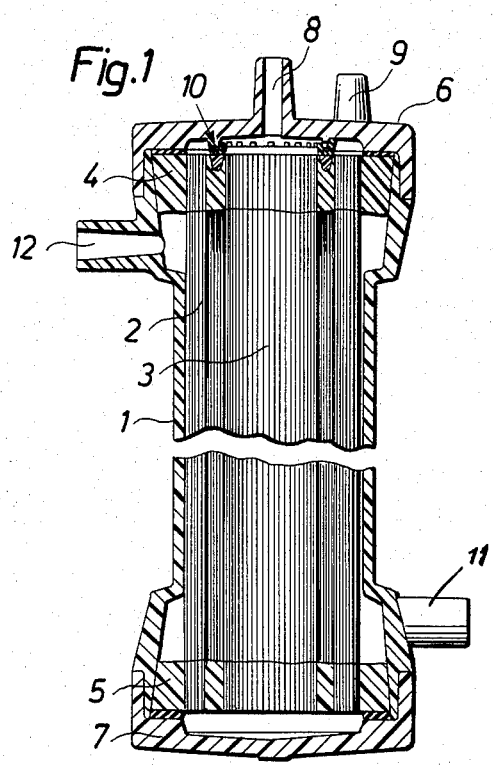
FIG. 1 is a side, elevational, partially sectional view of a one embodiment of a filtering device in accordance with the invention.

An example of a filtering device in accordance with the invention is shown in FIG. 1. The filtering device comprises a casing or a housing 1 with a great number of fibers arranged as two concentric bundles 2 and 3, respectively. These fibers are cast into two end walls 4 and 5, respectively, and open out on the outsides of these end walls. Covering the outside of end walls 4 and 5 and closing the casing 1 are outer covers 6 and 7, respectively. The outer cover 6 is provided with an inlet 8 and an outlet 9 for the filtered liquid. Between the inlet 8 and the outlet 9 is arranged a pressure-sensitive overflow valve 10. The design of this valve is shown on an enlarged scale in FIG. 2. The casing 1 is provided, moreover, with outlet 11 for the filtrate and, for reasons connected with manufacture, with second inlet 12 which may be used, for example, for the scavenging of the outsides of the fibers.

Figure 2:
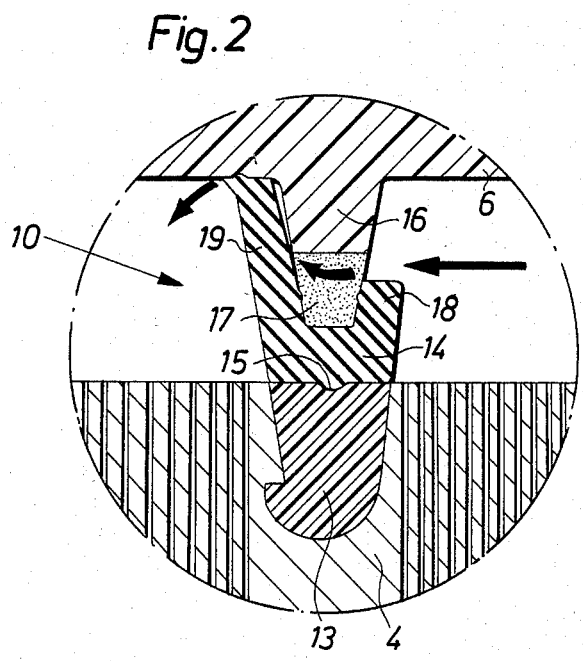
FIG. 2 is a side, elevational, cross-sectional view in enlarged detail of a portion of FIG. 1.

FIG. 2 shows the overflow valve 10 on a larger scale. The embodiment shown in this figure consists of a prop ring 13 cast into the end wall 4. An elastic U-shaped sealing ring 14 with a sealing bulge 15 rests against the prop ring 13. The sealing bulge 15 is shown in FIG. 2 in its original size, but in practice in its assembled condition, the bulge will be pressed almost completely into the sealing ring 14 itself. The ring 14 is slipped onto a fixed rigid flange 16 on the inside of the outer cover 6. This fixed flange 16 is provided with ports or openings 17 which are partly covered on one side (the side toward the inlet) by the flange 18 of the U-shaped sealing ring 14. The ports are wholly covered on their other side (the side toward the outlet for the filtered liquid) by the other flange 19 of this ring. This other flange 19 is thus longer and has an elasticity such that it is turned outwards when it is subjected on its inside to a suitably predetermined maximum pressure. In this manner, any exposure of the blood to hemolysis is prevented.

Figure 3:
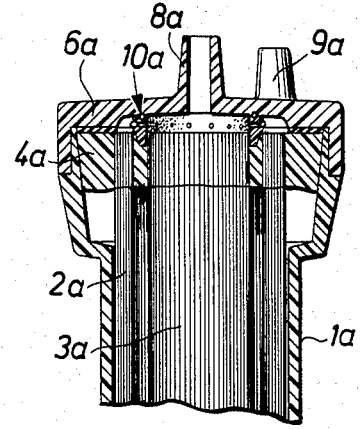
FIG. 3 is a side, elevational, partially cross-sectional view of another embodiment of a filtering device of the invention.
Figure 4:
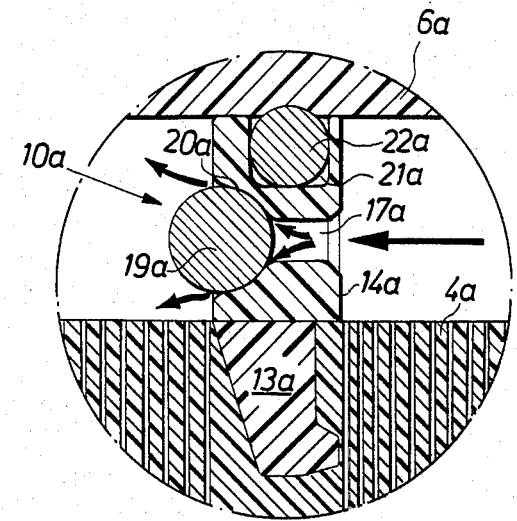
FIG. 4 is a side, elevational, cross-sectional view, in enlarged detail, of a portion of the FIG. 3.

In FIGS. 3 and 4 an alternative embodiment of the invention is shown. As this embodiment corresponds in principle with that according to FIGS. 1 and 2, the same reference numbers have been used but with the addition of the letter a. Thus, the casing is designated 1a and the concentrically arranged fiber bundles 2a and 3a. In the same manner, the end wall into which these fibers are cast is designated 4a, and the outer cover is provided with an inlet 8 and an outlet 9a for the filtered liquid and an overflow valve 10a arranged therebetween.

The overflow valve 10a is shown on a larger scale in FIG. 4. It consists of a prop ring 13a cast into the end wall 4a. The prop ring is attached in any suitable manner to fixed ring 14a, e.g., by glueing. The ring 14a is provided with radial ports or windows 17a. The outer openings of the ports (the side toward the outlet 9a) are covered by an elastic ring 19a. This ring 19a is arranged in a peripheral groove 20a which runs around the outside of the ring 14a. Moreover, the ring 14a is provided with an outer groove 21a with a sealing ring 22a arranged therein. This ring 22a seals against the adjoining outer cover 6a. The design according to FIGS. 3 and 4 functions in the same manner as that according to FIGS. 1 and 2, that is to say at a certain predetermined maximum pressure on the inside of the ring 14a, the ports 17a are opened owing to an expansion of the ring 19a.

Figure 5:
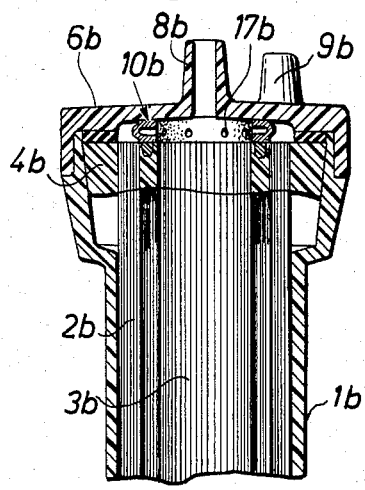
FIG. 5 is a side, elevational, partially cross-sectional view of yet another embodiment of a filtering device of the invention.
Figure 6:
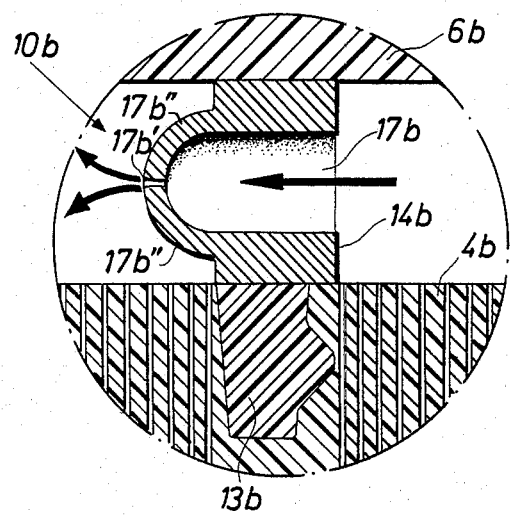
FIG. 6 is a side, elevational, cross-sectional view, in enlarged detail, of a portion of FIG. 5.

In FIGS. 5 and 6 an alternative embodiment is shown which in principle corresponds to that described above. For this reason, the same reference designations have been used, but with the addition of the letter b. Thus, the casing is designated 1b and the concentric fiber bundles enclosed therein 2b and 3b. These fiber bundles are cast into the end wall 4b on both sides of a pressure-sensitive overflow valve 10b. The numerals 8b and 9b designate an inlet and an outlet for the filtered liquid, respectively, in the cover 6b.

The overflow valve 10b is shown on a larger scale in FIG. 6. As in the overflow valves described above, it comprises a prop ring 13b which is cast into the end wall 4b. An elastic sealing ring 14b rests against the prop ring. The sealing ring is provided with a number of radial ports or openings 17b, which in the innermost part open out into an openable slit 17b'. The elastic ring 14b is adapted so as to be squeezed between the prop ring 13b and the outer cover 6b. The function is the same as for the designs described above. At certain maximum predetermined pressure on the inside of the ring 14b (the side toward the inlet 8b), the lips 17b" open so that the slit 17b' widens and allows the blood or any other liquid treated to pass therethrough to the outlet 9b for the filtered liquid.

Figure 7:
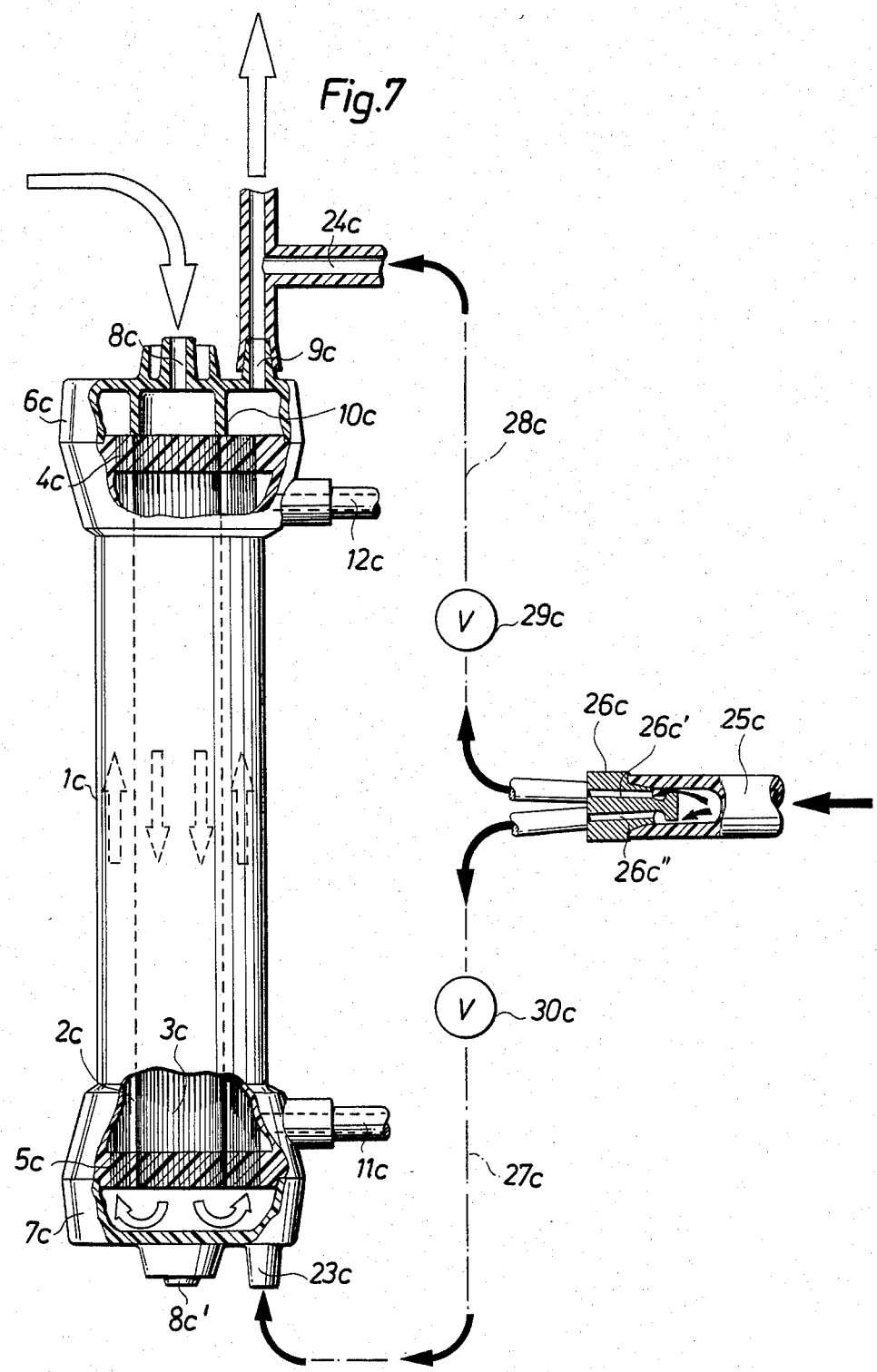
FIG. 7 is a side, elevational, partially cross-sectional, partially broken away view of yet another embodiment of a filtering device of the invention.
Figure 8:
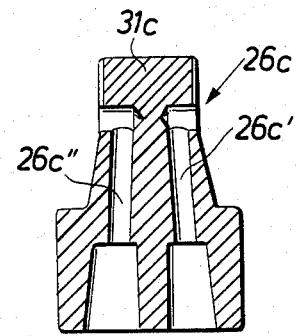
FIG. 8 is an enlarged, side, cross-sectional view of coupling shown in FIG. 7.
Figure 9:
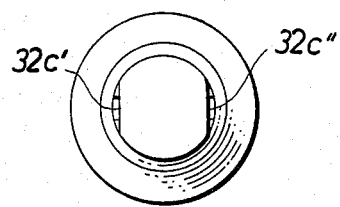
FIG. 9 is a front, elevational, cross-sectional view of the coupling shown in FIG. 7.

In FIGS. 7, 8 and 9 another alternative embodiment of the invention is shown. This embodiment includes means for the supply of replacement liquid. The means for supply of replacement liquid are described in greater detail in U.S. application Ser. No. 399,969, entitled "Filtering Device" filed by Kjell Hans Ingvar Christopherson, Thore Edvard Falkvall and Ulf Kenneth Matisson concurrently herewith on July 19, 1982, the disclosure of which is incorporated herein by reference. The design corresponds in principle to those described above and has been given, therefore, the same reference designations, but with the addition of the letter c. Thus, the casing is designated 1c and the fibers 2c and 3c, respectively. In the same manner, the end walls are designated 4c and 5c, respectively, and the outer covers 6c and 7c, respectively. Numeral 8c designates the inlet for the liquid, e.g., blood, to be filtered and 9c the outlet for the filtered liquid. Numeral 10c designates the overflow valve which in this case is considered to consist of a single thin flange attached to the cover 6c which yields elastically, if the pressure at the inlet 8c is above a predetermined maximum pressure. Numeral 8c' refers to a normally plugged up inlet corresponding to inlet 8c. This inlet 8c' is meant to facilitate possible scavenging of the fibers in connection with the manufacture of the device. Numeral 11c designates an outlet for the filtrate and 12c a further corresponding inlet or outlet, which may be plugged up and which has the same function, during the manufacture of the device, as the inlet 8c'.

The design in accordance with FIG. 7 differs from those described above primarily by an inlet 23c for the supply of replacement liquid between the two chambers formed by the fibers 2c and 3c, respectively. Furthermore, the construction is provided with a further inlet 24c for the supply of replacement liquid downstream of the chamber formed by the fibers 2c. The replacement liquid is supplied via a flexible tube 25c which with together with a coupling 26c forms a distributing valve. From this distributing valve, the replacement liquid is passed via the lines 27c and 28c to the inlets 23c and 24c, respectively. The liquid may pass the valves 29c and 30c, respectively. Either or both of these valves 29c and/or 30c can be controllable so that appropriate quantitites can be supplied to the desired inlet. The idea in principle is, however, that the distributing valve 25c–26c should be self-regulating. To achieve this, the ducts 26c' and 26c" are given appropriate dimension and the elasticity in the flexible tube 25c is chosen so that the inlet area is automatically increased for whichever duct 26c' or 26c" has the greatest back pressure.

In FIGS. 8 and 9, the coupling 26c is shown on a larger scale. As can be seen, the spigot 31c of the coupling is provided with two bevellings 32c' and 32c" at the sites of the openings of the ducts 26c' and 26c". Hence when the flexible tube 25c is slipped over the spigot 31c, a certain slight flow will take place via these bevellings. If an increase in pressure occurs in either line 27c or line 28c, an expansion of the flexible tube 25c will be obtained opposite the corresponding bevelling, so that the sectional area of flow increases, which makes possible a substantially unchanged flow.

It is evident from what has been said in the foregoing that the invention is intended primarily to be used for the manufacture of membrane filtering devices for hemofiltration and plasmapheresis and similar medical applications. However, it will be clear to those versed in the art, that the invention can also be applied to other cases where a filtration is desired at a relatively high pressure, which, however cannot exceed a predetermined pressure.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

What is claimed is:

1. A filtering device for filtering blood fluids comprising an inlet for said blood fluid, filtration means for filtering said blood fluid to provide a filtered blood fluid and a filtrate, said filtration means comprising two chambers connected in series, and including membrane material in each of said chambers, wherein said filtration takes place, a first outlet for the filtrate, a second outlet for the filtered blood fluid, and a pressure-sensitive valve between said inlet and said second outlet, said pressure sensitive valve having an elastically yieldable portion which is adapted to yield elastically to open a passageway between said inlet and said second outlet when the pressure at said inlet exceeds a predetermined pressure so that undesired pressure build-up beyond said predetermined pressure results in at least some of said blood fluid passing directly from said inlet to said second outlet without passing through said filtration means.

2. A filtering device in accordance with claim 1, wherein said two chambers are arranged in the same casing and wherein each chamber is formed of a number of interior spaces of thin-walled fibers.

3. A filtering device in accordance with claim 2, wherein the fibers of the two chambers are cast into two opposite first and second end walls of a cylindrical casing, wherein these two opposite first and second end walls are covered by respective first and second outer covers bearing said inlet and said second outlet for the filtered blood fluid, and wherein said inlet and said second outlet are arranged in said first outer cover and are separated by a seal arranged between the adjoining first end wall and said first outer cover, said seal constituting said pressure-sensitive overflow valve.

4. A filtering device in accordance with claim 3, wherein said seal is ring-shaped and is arranged substantially concentrically on the inside of said first outer cover pressing against the outside of said adjoining first end wall.

5. A filtering device in accordance with claim 4, wherein a prop ring is cast into said first end wall opposite said seal.

6. A filtering device in accordance with claim 5, wherein said seal consists of an elastic ring which is slipped onto a rigid flange fixed on the inside of said first outer cover.

7. A filtering device in accordance with claim 6, wherein said rigid flange is interrupted by one or more ports which are only partly covered on one side by said elastic ring and wherein said elastic ring, wholly but resiliently, covers the other side of the ports.

8. A filtering device in accordance with claim 7, wherein said elastic ring is of a U-shaped cross-section with one leg of said U-shape being longer than the other.

9. A filtering device in accordance with claim 4 or 5, wherein said seal is a fixed ring arranged between said first outer cover and the adjoining first end wall, wherein said fixed ring is provided with one or more radial ports, and wherein the outside of said ports is covered by an elastic ring on the outside said fixed ring.

10. A filtering device in accordance with claim 9, wherein said elastic ring is arranged in a peripheral groove in the fixed ring.

11. A filtering device in accordance with claim 9, wherein an elastic sealing ring is arranged between said first outer cover and said fixed ring to seal the fixed ring to said first outer cover.

12. A filtering device in accordance with claim 9, wherein said fixed rigid ring is attached to said adjoining first end wall or the prop ring cast into said adjoining first end wall.

13. A filtering device in accordance with claim 12, wherein said fixed rigid ring is attached by glue.

14. A filtering device in accordance with claim 4 or 5, wherein said seal is an elastic ring arranged between said first outer cover and said adjoining first end wall, said elastic ring comprising wall portions which adhere to one another at a first lower pressure, but which are adapted so as to be separated at a second predetermined higher pressure.

15. A method of filtering blood fluid comprising feeding said blood fluid through an inlet into a first chamber including membrane material for filtering said blood fluid and producing a partially filtered blood fluid and a filtrate therein, feeding said partially filtered blood fluid to a second chamber in series with said first chamber and including membrane material for further filtering said blood fluid and producing a filtered blood fluid and additional filtrate therein, withdrawing said filtered blood fluid through an outlet, providing a pressure-sensitive valve having an elastically yiedable portion between said inlet and said outlet, and causing said elastically yieldable portion of said pressure-sensitive valve to yield elastically to open a passageway between said inlet and said outlet when the pressure at said inlet exceeds an undesired pressure build-up at said inlet whereby at least a portion of said blood fluid may be passed directly directly from said inlet to said outlet without being filtered in either of said first or second chambers.

16. The method of claim 15 including reversing the direction of flow of said partially filtered blood fluid between said first and second chambers, whereby said first and second chambers are substantially parallel to each other and said inlet and said outlet are adjacent to each other.

17. A filtering device for filtering blood fluids comprising an inlet for said blood fluid, filtration means for filtering said blood fluid to provide a filtered blood fluid and a filtrate, said filtration means comprising two chambers connected in series, and including membrane material comprising thin walled fibers in each of said chambers, wherein said filtration takes place, a first outlet for the filtrate, a second outlet for the filtered blood fluid, a pressure-sensitive valve between said inlet and said second outlet so that undesired pressure build-up beyond a predetermined pressure at said inlet results in at least some of said blood fluid passing directly from said inlet to said second outlet, and a casing comprising opposite first and second end walls, wherein said fibers are cast into said first and second end walls of said casing, said two opposite second end walls being covered by respective first and second outer covers bearing said inlet and said second outlet for said filtered blood fluid, said inlet and said second outlet being arranged in said first outer cover and being separated by a seal arranged between the adjoining first end wall and said first outer cover, said seal constituting a pressure-sensitive valve.

18. A filtering device in accordance with claim 17, wherein said seal is ring-shaped and is arranged substantially concentrically on the inside of said first outer cover pressing against the outside of said adjoining first end wall.

19. A filtering device in accordance with claim 18, wherein a prop ring is cast into said first end wall opposite said seal.

20. A filtering device in accordance with claim 19, wherein said seal consists of an elastic ring which is slipped onto a rigid flange fixed on the inside of said first outer cover.

21. A filtering device in accordance with claim 20, wherein said rigid flange is interrupted by one or more ports which are partly covered on one side by said elastic ring and wherein said elastic ring, wholly but resiliently, covers the other side of the ports.

22. A filtering device in accordance with claim 21, wherein said elastic ring is of a U-shaped cross section with one leg of said U-shape being longer than the other.

23. A filtering device in accordance with claim 18 or 19, wherein said seal is a fixed ring arranged between said first outer cover and the adjoining first end wall, wherein said fixed ring is provided with one or more radial ports, and wherein the outside of said ports is covered by an elastic ring on the outside of said fixed ring.

24. A filtering device in accordance with claim 23, wherein said elastic ring is arranged in a peripheral groove in the fixed ring.

25. A filtering device in accordance with claim 23, wherein an elastic sealing ring is arranged between said first outer cover and a fixed ring to seal the fixed ring to said first outer cover.

26. A filtering device in accordance with claim 23, wherein said fixed rigid ring is attached to said adjoining first end wall or the prop ring cast into said adjoining end wall.

27. A filtering device in accordance with claim 26, wherein said fixed ring is attached by glue.

28. A filtering device in accordance with claims 18 or 19, wherein said seal is an elastic ring arranged between said first outer cover and said adjoining first end wall, said elastic ring comprising wall portions which adhere to one another at a first lower pressure, but which are adapted so as to be separated at a second predetermined higher pressure.

* * * * *